(12) United States Patent
Partain et al.

(10) Patent No.: US 7,660,384 B2
(45) Date of Patent: *Feb. 9, 2010

(54) CONTRAST-ENHANCED CONE BEAM X-RAY IMAGING, EVALUATION, MONITORING AND TREATMENT DELIVERY

(75) Inventors: Larry Partain, Los Altos, CA (US);
Stavros Prionas, Menlo Park, CA (US);
Edward Seppi, Portola Valley, CA (US);
Robert Sutherland, Menlo Park, CA (US); David Humber, Los Gatos, CA (US); Hassan Mostafavi, Los Altos, CA (US); Felix Fernando, Workingham Berks (GB); John Boone, Folsom, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/126,224

(22) Filed: May 23, 2008

(65) Prior Publication Data
US 2008/0226018 A1    Sep. 18, 2008

Related U.S. Application Data

(63) Continuation of application No. 11/437,076, filed on May 18, 2006, now Pat. No. 7,394,889.

(51) Int. Cl.
*A61B 6/04* (2006.01)

(52) U.S. Cl. .............................. 378/37; 378/4; 378/21; 378/65

(58) Field of Classification Search ................ 378/4–27, 378/37, 65, 68
See application file for complete search history.

(56) References Cited

U.S. PATENT DOCUMENTS

| | | | |
|---|---|---|---|
| 6,497,662 B2 | 12/2002 | Suurmond |
| 6,800,858 B1 | 10/2004 | Seppi |
| 6,888,919 B2 | 5/2005 | Graf |
| 6,987,831 B2 | 1/2006 | Ning |

(Continued)

OTHER PUBLICATIONS

J. Folkman, "Tumor Angiogenesis," Cancer Medicine, (2000) 5th Ed:134-137.

(Continued)

*Primary Examiner*—Jurie Yun
(74) *Attorney, Agent, or Firm*—Houst Consulting

(57) ABSTRACT

A method of imaging a patient's uncompressed region of interest using X-ray cone beam computed tomography or cone beam digital tomography comprises the step of introducing an effective amount of a contrast agent to the uncompressed region of interest. A system for imaging a patient's uncompressed region of interest using cone beam computed tomography (CBCT) or cone beam digital tomography (CBDT) comprises an X-ray source transmitting an X-ray to the uncompressed region of interest, an image acquisition system acquiring a plurality of two-dimensional projection images data for a CBCT or CBDT data set with at least one of the projection images acquired in 35 milliseconds or less, and a processor generating a three-dimensional computed tomography image data set resolving voxels with dimensions of 0.4 mm or less in at least two orthogonal directions.

16 Claims, 10 Drawing Sheets

U.S. PATENT DOCUMENTS

| | | | |
|---|---|---|---|
| 7,136,452 | B2 | 11/2006 | Spartiotis et al. |
| 7,394,889 | B2 * | 7/2008 | Partain et al. ............... 378/37 |
| 2005/0084060 | A1 | 4/2005 | Seppi et al. |
| 2006/0262898 | A1 | 11/2006 | Partain et al. |
| 2007/0030947 | A1 * | 2/2007 | Popescu .................. 378/19 |

OTHER PUBLICATIONS

J. Gisvold et al. "Computed Tomographic Mammography (CTM)" American Roentgen Ray Society (Dec. 1979) 133:1143-1149.

R. Jain, "Normalization of Tumor Vasculature: An Emerging Concept in Antiangiogenic Therapy", Science (Jan. 2005) 307:58-62.

R. Jain et al. "Dissecting Tumour Pathophysiology Using Intravital Microscopy" Nature Reviews, Cancer (Apr. 2002) 2:266-276.

K. Miles "Functional computed tomography in oncology" European Journal of Cancer (2002) 38:2079-2084.

J. Miller et al. "Imaging Angiogenesis: Applications and Potential for Drug Development" Journal of the National Cancer Institute (Feb. 2005) 97:172-187.

Y. Platonov et al. "High spectral resolution Al2O3/B4C, SiC/Si, SiC/B4C and SiC/C multilayer structures for the photon energies of 6keV to 19keV" X-Ray Sources and Optics (2004) 5537:161-170.

K. Smolenski et al. "Water-cooled multilayer optics for a wiggler beamline" SPIE, (1998) 3448:27-31.

C. Sturk et al. "Angiogenesis" The Basic Science of Oncology (2005) 4th Ed:244.

R. Sutherland, "Cell and Environment Interactions in Tumor Microregions: The Multicell Spheroid Model", Articles (Apr. 1988) 240:177-240.

U. Tateishi "Contrast-Enhanced Dynamic Computed Tomography for the Evaluation of Tumor Angiogenesis in Patients with Lung Carcinoma" American Cancer Society (Aug. 2002) 95:835-842.

I. Yeung "On-line Tumor Perfusion Measurement With Contrast Enhanced Cone Beam CT" Radiotherapy & Oncology, Journal of the European Society for Therapeutic Radiology and Oncology (Mar. 2006) 78:section 220, S77.

* cited by examiner

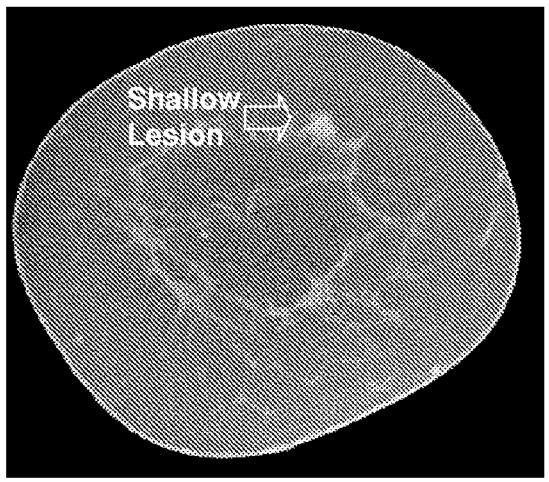 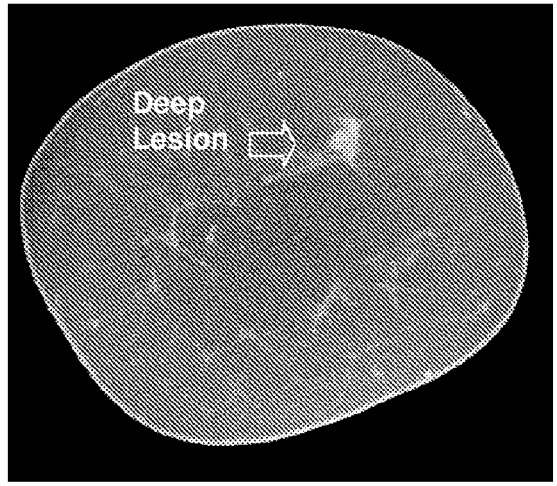
FIG. 3A (frontal slice)
FIG. 3B (frontal & deeper slice)
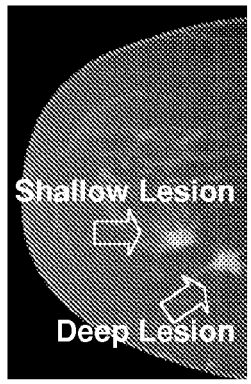
FIG. 3C (sagittal slice)

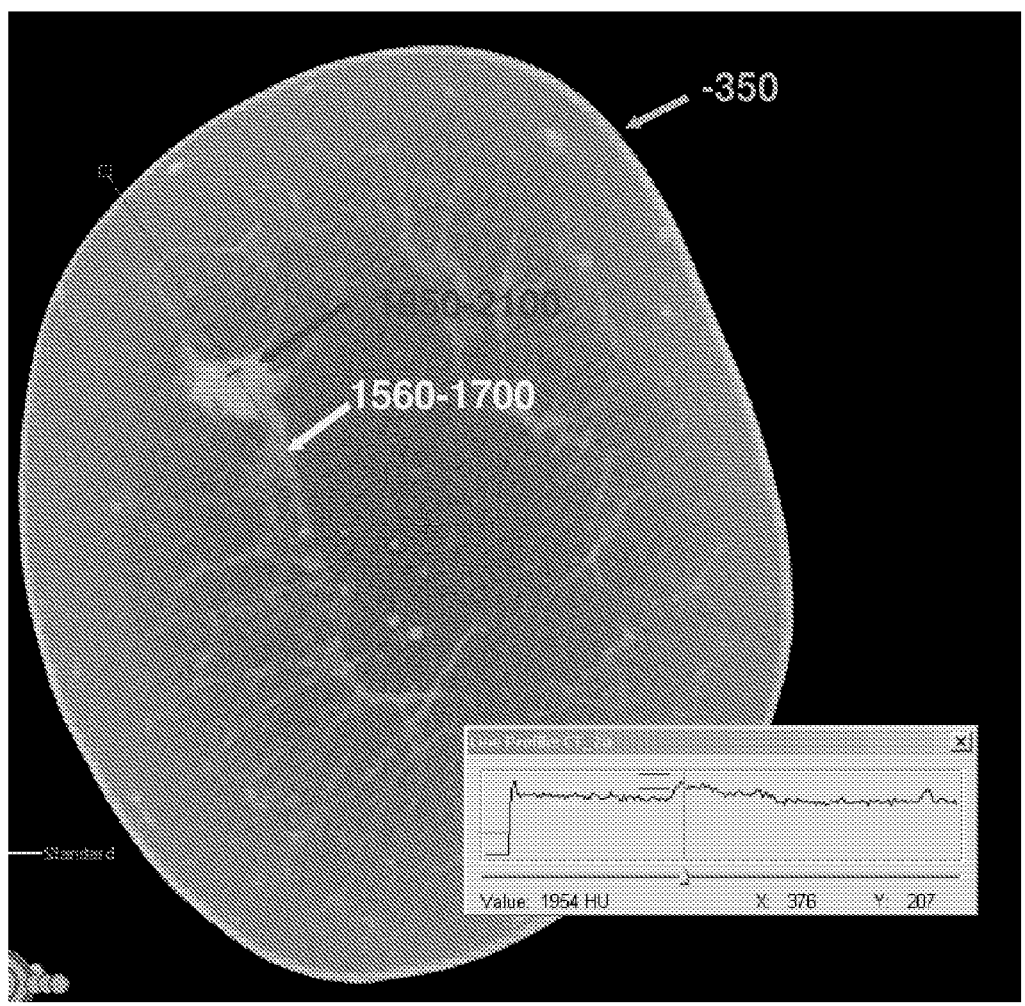
FIG. 4
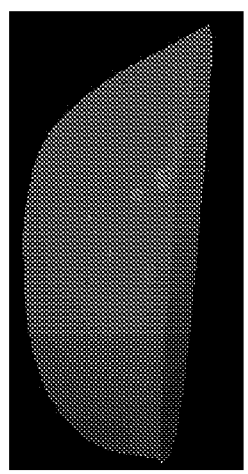 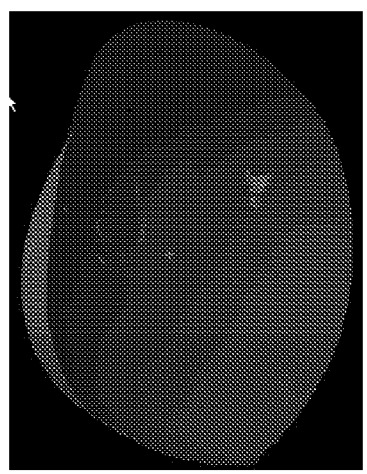 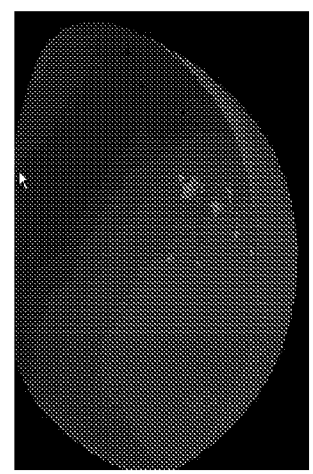 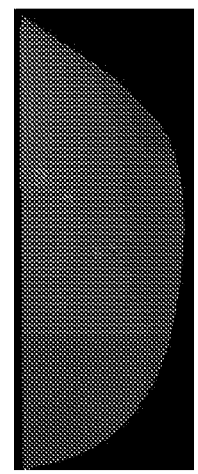
FIG. 5A          FIG. 5B          FIG. 5C          FIG. 5D

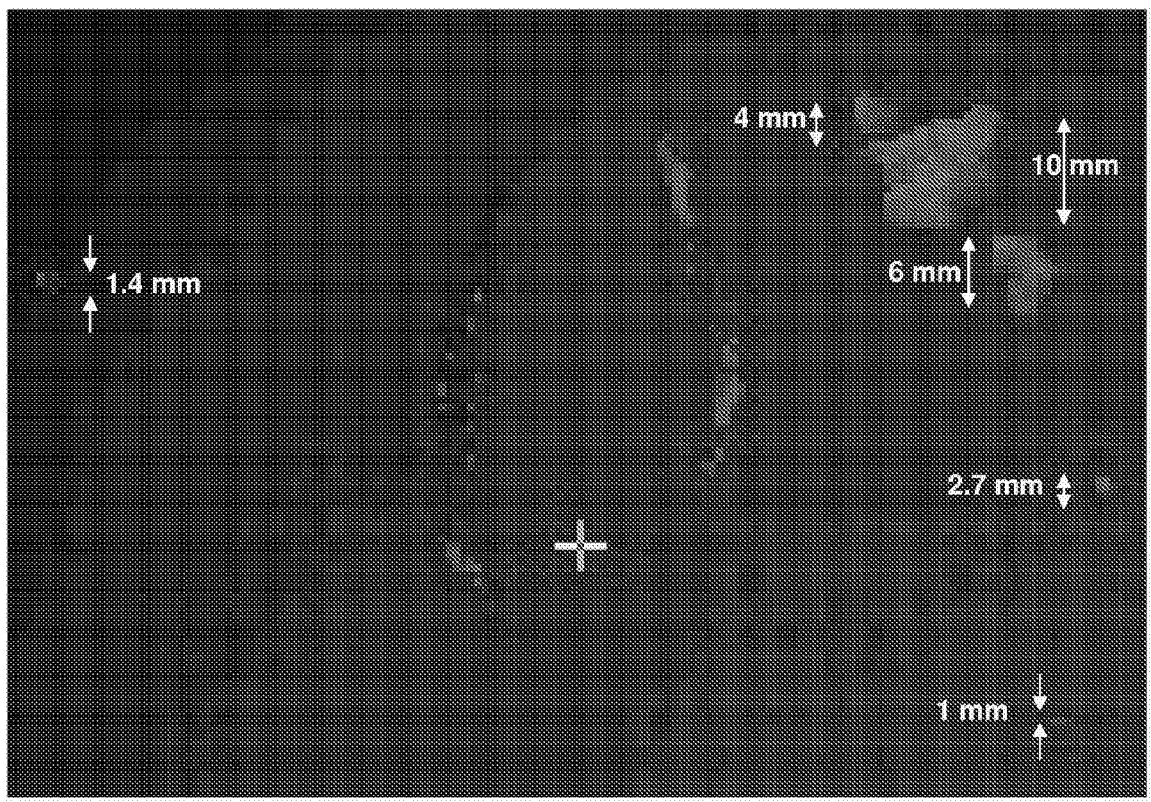
FIG. 6
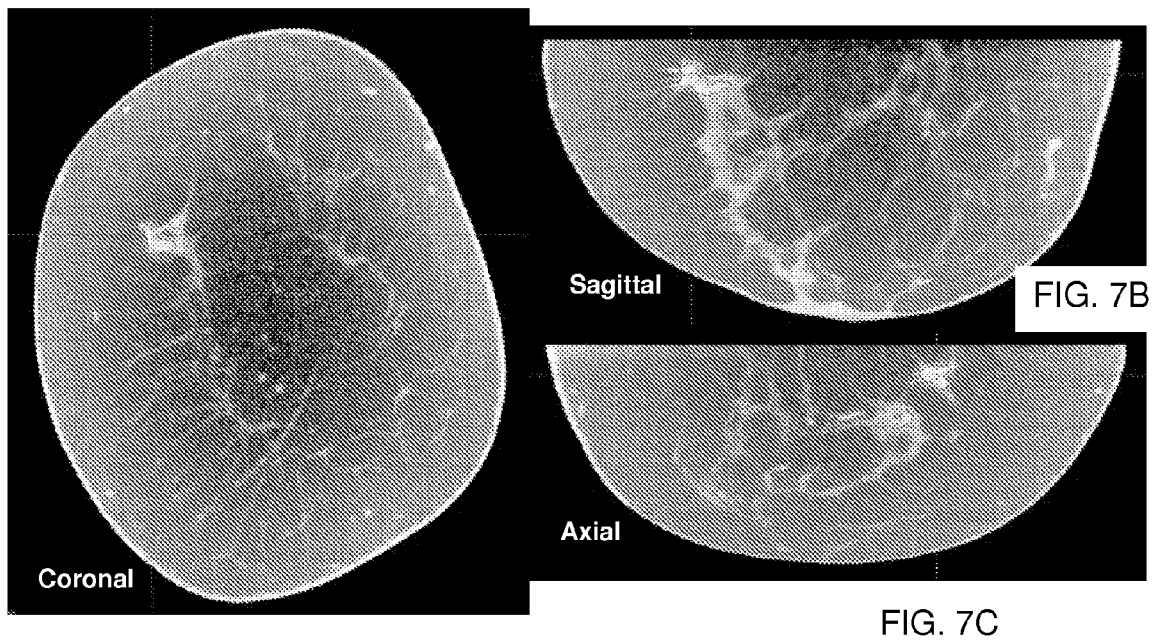
FIG. 7A
FIG. 7B
FIG. 7C

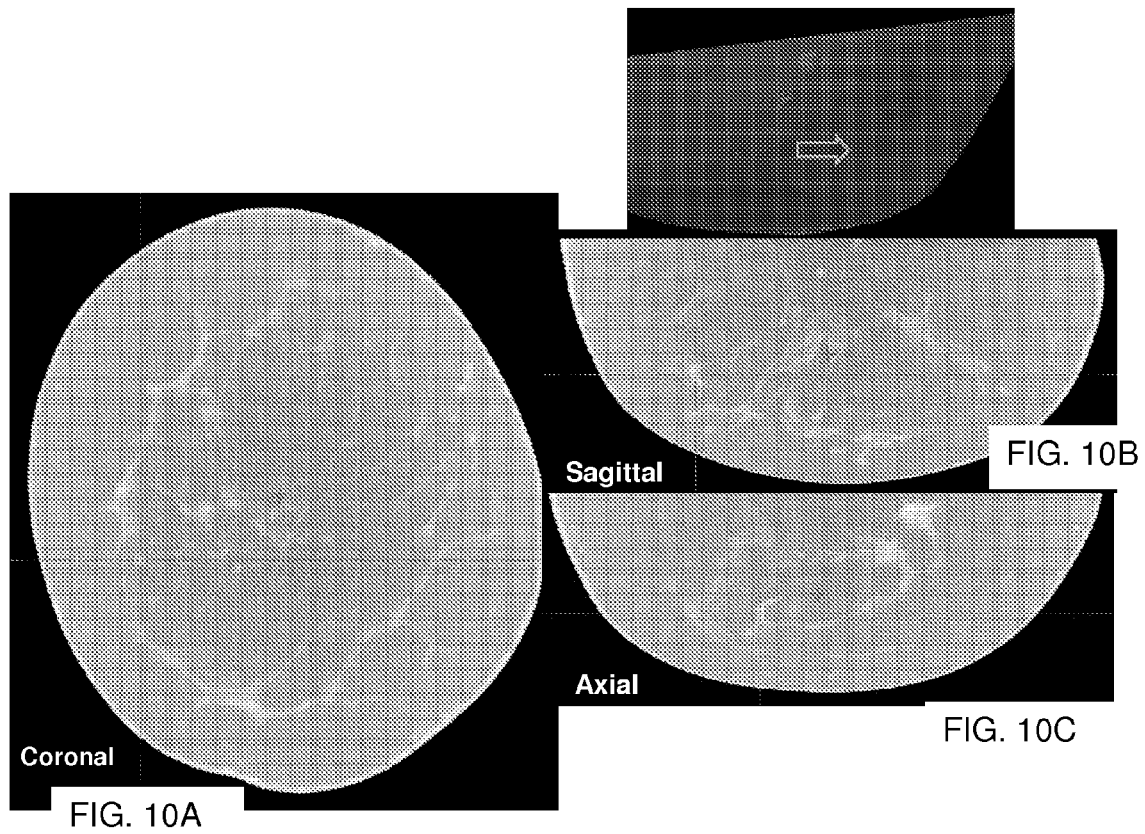

CONTRAST-ENHANCED CONE BEAM X-RAY IMAGING, EVALUATION, MONITORING AND TREATMENT DELIVERY

CROSS REFERENCE TO RELATED APPLICATIONS

This application is a continuation application of and claims priority to U.S. application Ser. No. 11/437,076 filed May 18, 2006, the disclosure of which is incorporated herein by reference in its entirety.

FIELD OF THE INVENTION

This invention relates generally to contrast-enhanced X-ray imaging, and in particular to contrast-enhanced cone beam computed tomography (CBCT) or cone beam digital tomosynthesis (CBDT) useful in detection, diagnosis, staging, monitoring, and treatment of cancer in human or animals.

BACKGROUND

Early detection and diagnosis are key for successful treatment of cancer such as breast cancer. Conventional X-ray mammography has been shown a cost-effective tool for early detection of breast cancer. However, the predictive value and specificity of X-ray mammography are limited due to projecting a three-dimensional anatomy into a two-dimensional image and due to poor contrast detectability. The minimum human cancer size that can be detected by conventional X-ray mammography has been on the order of 10 mm in diameter, weighing on the order of 1 gram and containing about $10^9$ cells. If the cancer starts from a single cell, it will undergo about 10 volume doubling times to reach a size of 10 mm in diameter. Ten further volume doubling times will lead to a tumor weighing about 1 kg with a size of 8-10 cm in diameter, which may be lethal. Currently only the latter 10 doubling times are typically observable in human. There is a need for a non-invasive procedure to explore the initial 10 doubling times since an initial latency period is believed to be followed by a rapid, exponential growth period that finally leads to a lesion with a size of about 10 mm in diameter, where the growth rate begins to decrease.

Gadolinium (Gd) contrast agents have been used with magnetic resonance imaging (MRI) in detection of breast cancer to enhance image contrast by detecting the Gd uptake in the cancer lesions and its washout profiles over time which are more sensitive than those of benign structures or lesions. Gd contrast-enhanced MRI has high sensitivity and can detect many breast cancer lesions missed or occult by conventional compression X-ray mammography. However Gd-MRI suffers from low specificity with many false positive findings, where a benign tissue is incorrectly identified as malignant. This is a problem shared with conventional compression X-ray projection mammography where about 75 percent of the biopsies of mammogram-identified suspicious regions turn out to be benign.

Cone beam CT has been used to provide three-dimensional images of patients' breasts. One problem with conventional cone beam CT is that the cancer lesions in the breast have about the same X-ray absorption coefficient and contrast level in CT slice images as the benign glandular tissue, which makes it difficult to differentiate the malignant lesions from benign structures, especially when the malignant lesions are adjacent to or combined with the glandular tissue. This is particularly a problem in younger women with denser breasts that are comprised heavily of glandular tissue.

Accordingly, there is a need for improved methods and systems for early detection, diagnosis and treatment of cancer throughout the bodies of humans or animals with high spatial and time resolutions.

SUMMARY OF THE INVENTION

In one aspect, a method of imaging a patient's uncompressed region of interest using X-ray cone beam computed tomography or cone beam digital tomography is provided comprising the step of introducing an effective amount of a contrast agent to the uncompressed region of interest.

In another aspect, a method of imaging a patient's uncompressed breast using X-ray computed tomography or digital tomography is provided comprising the step of introducing an effective amount of a contrast agent to the uncompressed breast.

In a further aspect, a system for imaging a patient's uncompressed region of interest using cone beam computed tomography (CBCT) or cone beam digital tomography (CBDT) is provided comprising an X-ray source transmitting an X-ray beam to the uncompressed region of interest, an acquisition system acquiring a plurality of two-dimensional projection images for a CBCT or CBDT data set, with at least one of the projection images acquired in 35 milliseconds or less, and a processor generating a three-dimensional computed tomography image data set resolving voxels with dimensions of 0.4 mm or less in at least two orthogonal directions.

In a further aspect, a method of delivering X-ray treatment dose distribution to a patient's uncompressed region of interest using X-ray cone beam computed tomography or cone beam digital tomography is provided comprising the steps of introducing an effective amount of a contrast agent to the uncompressed region of interest, acquiring a plurality of two-dimensional projection images for a cone beam tomography data set, and delivering an X-ray treatment dose distribution ranging from 1 to 7000 centigray to the uncompressed region of interest.

BRIEF DESCRIPTION OF THE DRAWINGS

These and various other features and advantages of the present invention will become better understood upon reading of the following detailed description in conjunction with the accompanying drawings and the appended claims provided below, where:

FIG. 3A is a coronal image of a patient's left breast with cancer lesions obtained using CBCT in accordance with one embodiment of the present invention;

FIG. 3B is another coronal image of a patient's left breast with cancer lesions obtained using CBCT in accordance with one embodiment of the present invention;

FIG. 3C is a sagittal image of a patient's left breast with cancer lesions obtained using CBCT in accordance with one embodiment of the present invention;

FIG. 4 is a coronal image of a patient's left breast with cancer lesions including a signal strength profile in accordance with one embodiment of the present invention;

FIGS. 5A-5D are surface-rendered, three dimensional (3D) images of a patient's left breast with cancer lesions obtained in accordance with one embodiment of the present invention;

FIG. 6 is a zoom-in view of a surface-rendered 3D image illustrated in FIG. 5C showing dimensions of the contrast-enhanced lesions in accordance with one embodiment of the present invention;

FIG. 7A is a coronal image of a patient's left breast showing highlighted boundaries of the contrast-enhanced lesions having dimensions of 10 mm and 4 mm identified in FIG. 6 in accordance with one embodiment of the present invention;

FIG. 7B is a sagittal image of a patient's left breast showing highlighted boundaries of the contrast-enhanced lesions having a dimension of 10 mm identified in FIG. 6 in accordance with one embodiment of the present invention;

FIG. 7C is an axial image of a patient's left breast showing highlighted boundaries of the contrast-enhanced lesions having dimensions of 10 mm and 6 mm identified in FIG. 6 in accordance with one embodiment of the present invention;

FIGS. 10A-10C are coronal (FIG. 10A), sagittal (FIG. 10B) and axial (FIG. 10C) images of a patient's left breast showing two orthogonal lines crossing the approximate center of the 1.4 mm contrast-enhanced lesion in accordance with one embodiment of the present invention, with the upper right portion of FIG. 10 being one view of the volume rendered set illustrated in FIG. 5, where the pink block arrow points to the feature centered in the cross-lines of FIGS. 10A-10C;

DETAILED DESCRIPTION OF THE INVENTION

Various embodiments of the present invention are described hereinafter with reference to the figures. It should be noted that some figures are schematic and the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. For instance, in the following description, the present invention is described with embodiments of cone beam computed tomography. It will be appreciated that the claimed invention may also be used with other X-ray imaging systems such as cone beam digital tomosynthesis, and inverse-geometry volumetric computed tomography (IGVCT) which is not cone beam based. Further, in the following description, the present invention is described with embodiments where a patient's breast is investigated. It will be appreciated that the claimed invention can be used in examination of not only human patients and any of their parts, but also living animals and plant of any size, including a region of interest which is nourished and supported to maintain life-like behaviors during extended studies, and a region of interest which is placed in another living host or into a support environment like a Petri dish with a growth medium.

Figure 1:
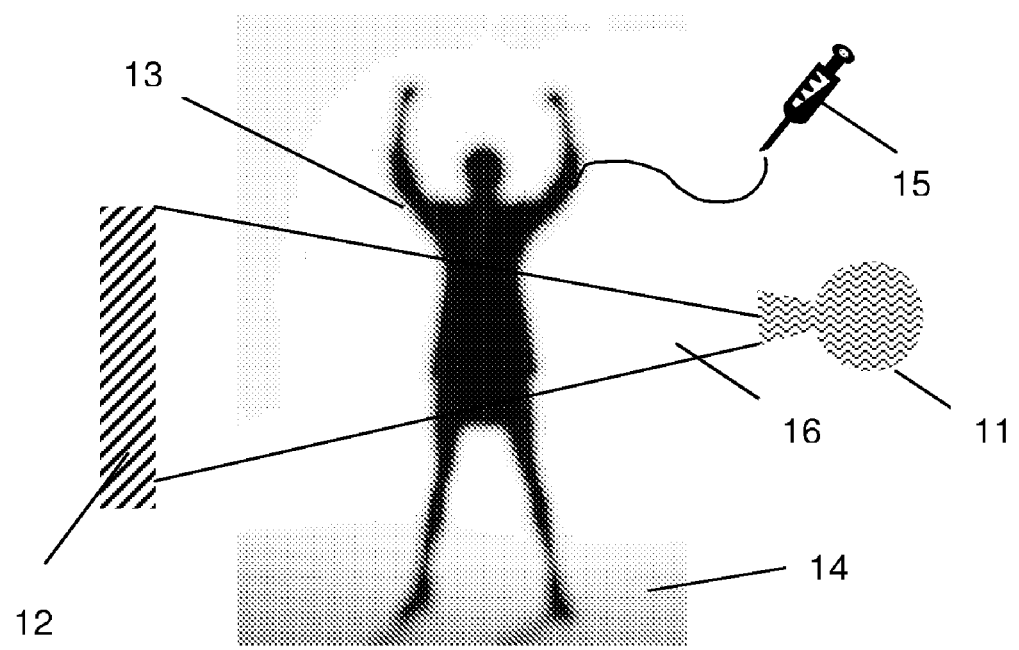
FIG. 1 is a schematic diagram illustrating an X-ray imaging system in accordance with one embodiment of the present invention.

FIG. 1 illustrates an X-ray imaging system 10 in accordance with one embodiment of the present invention. The X-ray imaging system 10 includes an X-ray source 11 and a detector 12. Between the X-ray source 11 and detector 12 is an object 13 to be examined. The object 13 is supported by a structure 14 and can be in any position and/or orientation suitable for imaging. An injection device 15 is provided to introduce an effective amount of a contrast agent to a region of interest in the object 13.

The X-ray source 11 generates and transmits an X-ray beam 16 to the region of interest in the object 13. The X-ray detector 12 receives and detects the X-ray beam passing through the region of interest. The X-ray beam 16 is converted to electrical signals (pixel values) representing the intensity of the X-ray beams passing through the region of interest. The electrical signals may be reconstructed using an algorithm known in the art to produce two or three dimensional images of the region of interest.

The X-ray source 11 is capable of generating X-ray beams at different energy levels. The X-ray source 11 may include a single beam generation module or multiple beam generation modules (not shown). In accordance with a specific embodiment of the present invention, the radiation source 11 is configured to generate X-ray beams at a kilo-electron-volt (keV) energy level and a mega-electron-volt (MeV) energy level. A keV energy level X-ray beam is generally used for forming images of cancer and/or tissues in patient, and is therefore also referred to as an image beam or a diagnostic beam. A MeV energy level X-ray radiation beam is generally used for targeting and treating tumor or other abnormal tissue in patient. The MeV energy level X-ray radiation beam can also be used for forming images of patient. However, images formed using an MeV energy level X-ray beam typically have lower contrast and spatial resolutions than those formed with an X-ray beam at a lower energy level, e.g., keV energy level. The MeV energy levels have the advantage that they reduce CT image artifacts, like rings and rays, generated by dense regions of patient anatomy, like bones and metal implants. In accordance with one embodiment of the present invention, the X-ray source 11 includes two X-ray beam generators, one for generating the keV energy level X-ray image beams and another for generating the MeV energy level X-ray radiation beams. The two beam generators may be located in close proximity with each other or separated from each other. For example, in one specific embodiment, the two beam generators are so located that they transmits radiation beams toward a patient's breast at an angle of approximately 90 degree from each other. In accordance with another embodiment, X-ray source 11 includes a signal X-ray beam generator that is capable of generating X-ray beams at multiple energy levels. An embodiment uses dual (e.g. keV and MeV) energies to provide additional medically relevant information. By way of example, U.S. Pat. No. 6,888,919 issued on May 3, 2005 entitled "Radiotherapy Apparatus Equipped with an Articulable Gantry for Positioning an Imaging Unit" discloses a system with X-ray radiation sources at different energy levels, the disclosure of which is incorporated herein by reference in its entirety.

Detector 12 is capable of detecting X-ray beams passing through the region of interest at both the MeV high energy level and the keV low energy level. In some embodiments, the detector 12 includes two image detecting devices and, one for detecting images formed by the keV image beams, and the other for detecting images formed by the MeV radiation beams. In some embodiments, detector includes a single image detecting device that is capable of detecting images formed by beams at multiple energy levels. By way of example, U.S. Pat. No. 6,800,858 issued Oct. 5, 2004 entitled "X-Ray Image Acquisition Apparatus" discloses an X-ray image detecting device that is capable of detecting multiple energy level X-ray images and can be used as detector in accordance with the present invention. U.S. Pat. No. 6,800, 858 is incorporated herein by reference in its entirety.

In some embodiments, the detector 12 is a two dimensional flat panel X-ray sensor. In some embodiments, the detector 12 is a photon counting flat plate image sensor. The photoconductor films comprised of the photon counting flat plate image sensor include polycrystalline mercuric iodide, lead iodide and thallium bromide and amorphous selenium. The photoconductor films may be deposited by physical vapor deposition or by screen printing or casting powders of these materials with binders and solvent (particle-in-binder-technology) onto pixilated arrays of amorphous silicon thin film transistor switches and data storage capacitors at each pixel. The latter are run in the signal integration mode at a fast frame rate such that normally only one X-ray photon per frame is detected at each pixel so that this pixel's signal strength is an approximate or rough measure of the incident photon's energy. Each pixel's electrode structure can be adapted for best photon-counting behavior, including the use of inter digitated back contacts held at different voltage potentials.

In some embodiments, the photon counting flat plate image sensor comprises single crystal X-ray detectors of cadmium telluride, cadmium zinc telluride, mercuric iodide or lead iodide operable at both room temperature and at reduced temperatures. As used herein, single crystal X-ray detectors specifically include cadmium zinc telluride. Each single crystal may have a cross sectional area of about 1 mm$^2$ or less for good spatial and enough depth to absorb >80% of the incident X-ray photons (depths on the order of 0.6 mm for ~100 keV photons and on the order of 1 cm for 6 MeV photons). These single crystal elements can be tiled into an array (e.g., 20 rows by 20 columns) and each connected to pulse height counting electronics, including separate electronics for each pixel, and arrays of such electronics constructed as application specific integrated circuits (ASICs). This array can either be used alone or placed beside the non-photon-counting arrays (with sub-millimeter spatial resolutions) so that the photon counting data is obtained simultaneously with the non-photon-counting imagers.

In one specific embodiment, the detector 12 is a photon counting flat plate image sensor having 1536×2048 rows and columns of square pixels measuring 194 m on a side. In some embodiments, the detector 12 is operated at 1 frame per second in acquiring projection images. In some embodiments, the detector 12 can be operated at 10 frames per second or higher. In some embodiments, the detector 12 can be operated at 1000 frames per second or higher.

In some embodiments, an image acquisition apparatus including a photon counting flat plate image sensor acquires multiple two-dimensional projection images for a cone beam computed tomography data set where one or more of the projection images are acquired in 5 seconds or less. In some embodiments, the image acquisition apparatus acquires multiple two-dimensional projection images for a cone beam computed tomography data set where one or more of the projection images are acquired in 35 milliseconds or less. In some embodiments, the image acquisition apparatus acquires multiple two-dimensional projection images for a cone beam computed tomography data set where one or more of the projection images are acquired in 0.1 milliseconds or less.

Structure 14 supports the patient 13 in a suitable position and/or orientation for imaging. The structure 14 may be constructed in various configuration such that the patient 13 can lie side ways, or lie prone or supine on the top of the structure 14. The structure 14 may also be constructed in various configuration such that the patient can stand or sit leaning against the structure 14 and extending only a region of interest such as a breast through the structure for imaging. Structure 14 may also perform the function of protecting the rest of the patient's body from direct X-ray exposure. Structure 14 may be made of X-ray absorbing materials such as materials containing lead, tungsten, tantalum, uranium, thorium, iridium, gold, and their alloys or mixtures.

In some embodiments, the structure 14 is constructed in such way that a region of interest such as a breast is supported uncompressed. As used herein, the term "uncompressed region of interest" or "uncompressed breast" refers to a region or breast that is not squeezed or confined in a manner that reduces the transport of body fluids or introduced agents. Uncompressed embodiments include support and positioning platforms, flat and curved surfaces, cups, cylinders, and bras (including fabric and plastic compositions). Uncompressed embodiments specifically include configurations that enhance the transport of body fluids and introduced agents, such as a cylinder with one open end, placed over a breast, and pumped down to partial vacuum. The embodiments with uncompressed region of interest or breast are desirable since they not only eliminate the pain suffered by patients in conventional compressed mammography, but also facilitate effective circulation of contrast agents in the uncompressed region of interests or breasts to assist assessing suspicious lesions.

In one specific embodiment, the patient 13 lies prone on the support structure 14. The patient's the left breast, the region of interest, extends down through a hole in the support structure 14 into the X-ray beam 16 from the X-ray source 11 so that X-ray projection images can be obtained on the detector 12 with little direct X-ray beam exposure to the patient's heart and lungs.

In another specific embodiment, the structure 14 is constructed to be able to rotate 180 degrees plus the X-ray beam fan angle. The X-ray source 11 and the detector 12 are attached to a C-arm that remains fixed in place. The X-ray cone beam can be sliced in half so that only the patient's breast is directly exposed and the heart and lungs are not directly in the beam path.

In another specific embodiment, the patient 13 is in a leaning upright position and resting on a rolling stool with an angled or vertical support structure. The X-ray source 11 and the detector 12 are connected together on a C-arm that rotates around the patient to acquire the cone beam CT data. The X-ray beam may have a half cone shape so that on the breast but not the heart and lungs are exposed to the direct X-ray beam.

In a further specific embodiment, the patient 13 lies horizontally and sideways to expose just parts of the anatomy to the direct X-ray beam. Either the support structure 14 or the C-arm holding the X-ray source 11 and the flat panel imager 12 can rotate, or both can rotate.

In a further specific embodiment, the support structure 14 is constructed such that the shoulder region can extend into the half-fan X-ray beam to image the region from the breast up into the arm pit.

In another specific embodiment, the structure 14 is a support couch and the patient 13 can lie on it. The X-ray source 11 and detector 12 are mounted inside an enclosure of a ring gantry so that any part of the patient's anatomy can be imaged. Alternatively, an un-enclosed C-arm holds the X-ray source 11 and the detector 12 and rotates both the X-ray source and detector around the patient 13.

U.S. patent application Ser. No. 11/134,695 filed May 20, 2005 entitled "System and Method for Imaging and Treatment of Tumorous Tissue in Breasts Using Computed Tomography and Radiotherapy" discloses various structures that can be used to support uncompressed breasts during X-ray imaging. U.S. patent application Ser. No. 11/134,695 is incorporated herein by reference.

The injection device 15 can be any suitable device that administers an effective amount of a contrast agent to the region of interest. By way of example, a syringe can be used with a flexible tube to inject a contrast medium to a patient's vein such as in the arm, which is then circulated to the patient's region of interest via the circulation system.

The contrast agents used in the present invention can be any substances that alter the contrast of images by affecting the attenuation of X-rays. The contrast agent can be a positive contrast medium that absorbs X-rays more strongly than the tissue or structure being examined, or a negative contrast medium, less strongly. By way of example, the contrast agent can be iodine-based or gadolinium-based. Examples of iodine-based contrast agents include but are not limited to Visopaque (iodixanal, GE Healthcare), omnipaque (iohexol, GE Healthcare), Ultravist (iopromide, Berlex), or isovue (iopamidol, Bracco Diagnostics). Other contrast agents exist, these are examples. Examples of gadolinium-based contrast agents include but is not limited to MultiHance (gadobenate dimeglumine, Bracco Diagnostics), Omniscan (GE Healthcare), or Magnevist (Berlex Laboratories). Preferably, the contrast agents used in the present invention include any iodine based contrast agent with high concentration, such as 300 milligrams of iodine per ml or above. In a specific example, the contrast agent used in the present invention is Visopaque.

The effective amount of the contrast agent depends on the location in the patient's body region being imaged, the location of the contrast injection site relative to the heart, the size and weight of the patient, the physical condition of the patient, the patient's position, and can be determined by attending technician. In general, the effective amount of the contrast agent is in the range from 50 to 150 ml.

In operation, image acquisition starts after the injection of the contrast agent. The time delay between the injection of the contrast agent and the image acquisition depends on the lesion type, size and the individual characteristics such as cardiac output. In one embodiment where a human breast is to be examined, it is preferable to start image acquisition approximately 40 to 130 seconds after the injection of a contrast agent into the patient's vein. In another embodiment, a total of 100 ml of contrast agent is injected into the patient's brachial vein at 4 ml per second for 25 seconds, and imaging commences 90 seconds after the start of contrast injection.

One method for defining an optimal time delay between injection of the contrast agent and image acquisition is to study a large group of patients, who are going to receive external beam radiotherapy, and then continually measure cone beam CT data sets from the start of the contrast agent injection to 10 minutes or beyond. From this study, guidelines can be produced for image acquisition delay times as a function of lesion type and size and as a function of individual characteristics like cardiac output. Another method for defining optimal delay times is to repeat the above procedure using CBDT or fast CBCT. With the resulting seconds (down to milliseconds) time resolutions (particularly for CBDT), the full time delay period from the start of contrast agent injection to 10s of minutes and beyond can be quickly sampled for brief time intervals throughout the total period using a much smaller fraction of time when X-rays would be exposing the patient during CBDT data acquisition. For example, the first data acquisition time can start at 1 second and then continuously double the times until the next acquisition to 2, 4, 8, 16, 32, 64, 128 seconds and so on, until the total desired sampling time span has been covered out to 10 to 30 total minutes or beyond. When any one of these intervals is shown to be desired, the follow-up study can fill in many more acquisitions intervals, into the one or more of initial intervals identified as special interest. An alternate timing sequence for a slower acquisition system can be an initial sampling delay of 30 seconds to the first data acquisition and then a sequence of additional acquisition delay interval lengths of 17, 34, 68, 136 and 272 seconds and so on, as desired.

The relative motion among the X-ray source 11, the detector 12, and the patient 13 is provided to obtain multiple high frame rate projection images that are sufficient to acquire the data needed to reconstruct computed tomography slice images of the region of interest. For cone beam computed tomography (CBCT), the relative spacing and orientation of the detector to the X-ray source is kept rigidly constant as relative motion is provided between them and the patient. Typically this is a relative rotational motion in a plane around the patient's region of interest for either 180 degrees plus the cone angle of the X-ray beam or for 360 degrees plus a few degrees such as +~5-10 degrees to provide needed overlap. For cone beam digital tomosynthesis (CBDT), the relative motions among the detector, the X-ray source, and the patient is much more general and arbitrary but with the condition that the pathways of the X-ray photons of the cone shaped X-ray beam pass through every voxel of the patient's region of interest at a variety of angles and be detected by the detector in the form of projection images. Generally, the larger the range of angles through each voxel, the better the spatial resolution will be, subject to the limitations imposed by the detector resolution and X-source spot size. The bigger the number of separate projections images containing data on that voxel, the clearer (higher signal-to-noise ratio) image and more accurate the measured absorption coefficient and contrast will be for each voxel. CBDT specifically includes circular rotation between the X ray source 11 and detector 12 and the object 13, where the total angle of rotation is less than 360 degrees, such as 300, 260, 220, 200, 180, 160, 140, 120, 100, 80, 60, 40, 20, and 10 total rotation degrees or less. In imaging three dimensional volumes, the smallest volume (often a cube) that can be resolved is referred to as a voxel. The term voxel is an extension of the term pixel which is the smallest area (typically square) that limits the resolution of 2D projection images. One major advantage of computed tomography is that a 2D image can be reconstructed by assembling the contrast values (X-ray absorption coefficients) of only those voxels that lie in this image plane. All of the confusing contrast of planes above and below are removed, unlike single projection images that have all of the separate plane images superimposed.

In some embodiments, the 2D projection images are reconstructed to 3D CT image data set resolving voxels with dimensions of 10 mm or less in at least two orthogonal directions. In some embodiments, the 2D projection images are reconstructed to 3D CT image data set resolving voxels with dimensions of 0.4 mm or less in at least two orthogonal directions. In some embodiments, the 2D projection images are reconstructed to 3D CT image data set resolving voxels with dimensions of 5 microns or less in at least two orthogonal directions.

In one working example, a patient 13, whose left breast was the region of interest, lay prone on the support structure 14. The breast extended down through a hole in the support structure 14 into the X-ray beam 16 from the X-ray source 11. The breast was uncompressed. X-ray projection images were obtained on a high spatial resolution flat plate image sensor 12 having 1536×2048 rows and columns of square pixels measuring 194 μm on a side. This flat plate image sensor 12 is available from Varian Medical Systems, Inc. in Palo Alto, Calif. The patient's heart and lungs were protected from direct X-ray beam exposure by the support structure 14. The X-ray source 11 and flat plate image sensor 12 were rigidly connected on an arm that rotated about 365 degrees around the stationary patient 13 in 16.6 seconds using an imaging rate of 30 frames per seconds to collect 500 projection images of the patient's left breast.

Figure 2:
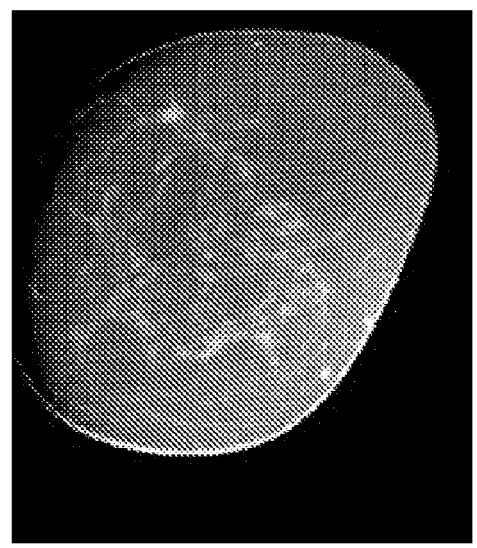
FIG. 2 is a coronal image of a healthy patient's left breast obtained using CBCT in accordance with one embodiment of the present invention.

FIG. 2 is a coronal image of a healthy patient's left breast obtained by the above example. As shown in FIG. 2, a fine spatial resolution detail was obtained in a CBCT configuration. The whiter portions in the image are the glandular tissue distributed throughout the breast and the skin boundary. The darker portions are the adipose or fat regions of the breast. Each of the 500 projection images, used to create the total cone beam CT data set, reconstructed to give the FIG. 2 slice image (as well as all the sets used for the FIGS. 3-12 slice image reconstructions), was acquired in about 33 milliseconds, for a total cone beam CT data acquisition time of 16.6 sec. The projection images (and all the other data used for FIGS. 3-12) were obtained with a single X-ray energy spectra of 80 kVp.

The same CBCT procedure was repeated with another patient having the highest and worst rating for breast cancer of BIRADS 5. 100 cc Visopaque (iodine-based contrast agent) was injected in 4 seconds into the vein of the patient's arm. 140 seconds after the patient was injected with Visopaque, 500 rotating projection images were taken. FIGS. 3A-3C show reconstructed CBCT coronal and sagittal images of the patient's left breast using a Feldkamp reconstruction algorithm.

FIGS. 3A and 3B are coronal images showing two lesions that have enhanced contrast, at two increasing depths into the breast, as indicated with two arrows. FIG. 3C is a sagittal image showing both contrast-enhanced lesions in a single image. Subsequent surgical biopsy confirmed that the two contrast-enhanced lesions were indeed malignant. With conventional projection X-ray compression mammograms without contrast enhancement, only the larger and deeper of the two lesions could be identified.

A signal strength profile along a red line is shown as an insert in FIG. 4, starting from beyond the skin line extending through the middle of the larger lesion of FIG. 3B and then on deeper into the breast volume. The contrast-enhanced region has signal count values from 1850 to 2100, while the glandular tissue has count values from 1560 to 1700. Just beyond the skin line, the count value drops into the negative region. These count values are scaled and offset experimental data count levels and are not calibrated Houndsfield unit values. By assigning different colors to different count values, surface-rendered 3D perspective images can be obtained. For example, colors of pink can be assigned to a skin count value of $-350$, of green to glandular count values between 1560 and 1700, and of red to contrast-enhanced count values between 1850 and 2100. The surface-rendered 3D perspective images are shown in FIGS. 5A-5D. These images were generated using a computer software Eclipse™ available from Varian Medical Systems, Inc. in Palo Alto, Calif.

The rendered surface of the skin (shown as semi-transparent pink) forms a bowl. FIG. 5A shows a side view and 5B to 5D show additional rotational views, looking from the back (i.e. the chest wall) toward the front. As shown in FIGS. 5A-5D, two large volumes and four additional discrete small volumes are resolved to have the enhanced contrast. A zoomed view of the six contrast-enhanced volumes are shown in FIG. 6.

The largest contrast-enhanced volume of FIG. 6 has a linear dimension of approximately 10 mm, the smallest sized cancer lesion that can typically be seen in traditional projection image screening X-ray mammograms. All the other contrast-enhanced volumes' dimensions are scaled to that of the largest. Both the 10 mm lesion and the 6 mm lesion were confirmed with biopsies to be malignant cancers.

Earlier detection and treatment are key for treatment of breast and other cancers. Cancer growths are among the causes that can give such contrast-enhanced regions and these resolved volumes go down to sizes of the order of 1 mm, with 1000 times less volume than that of the 10 mm wide lesion. Such 1 mm linear dimensions' growths are on the order of the sizes of nascent cancer foci (R. Sutherland, Science, Vol. 240, pp. 177-240, 1988) before they grow large enough to begin causing significant problems. This level of resolution comes directly from the approximately cubic voxel size of about 400 μm on a side of the X-ray CBCT reconstruction. A traditional approach in standard mammogram screening when suspicious regions ($\geq 10$ mm) are found in the images is to repeat the image in 6 months to look for changes, including rapid growth, a strong confirming indicator of cancer. With the improved method of the present invention, potential cancer lesion volumes are identifiable at much smaller sizes for earlier detection, and their changes including size is confirmable over much smaller repeat times (e.g. weeks to a month) for earlier confirmation of malignancy.

Figures 8A, 8B, 8C:
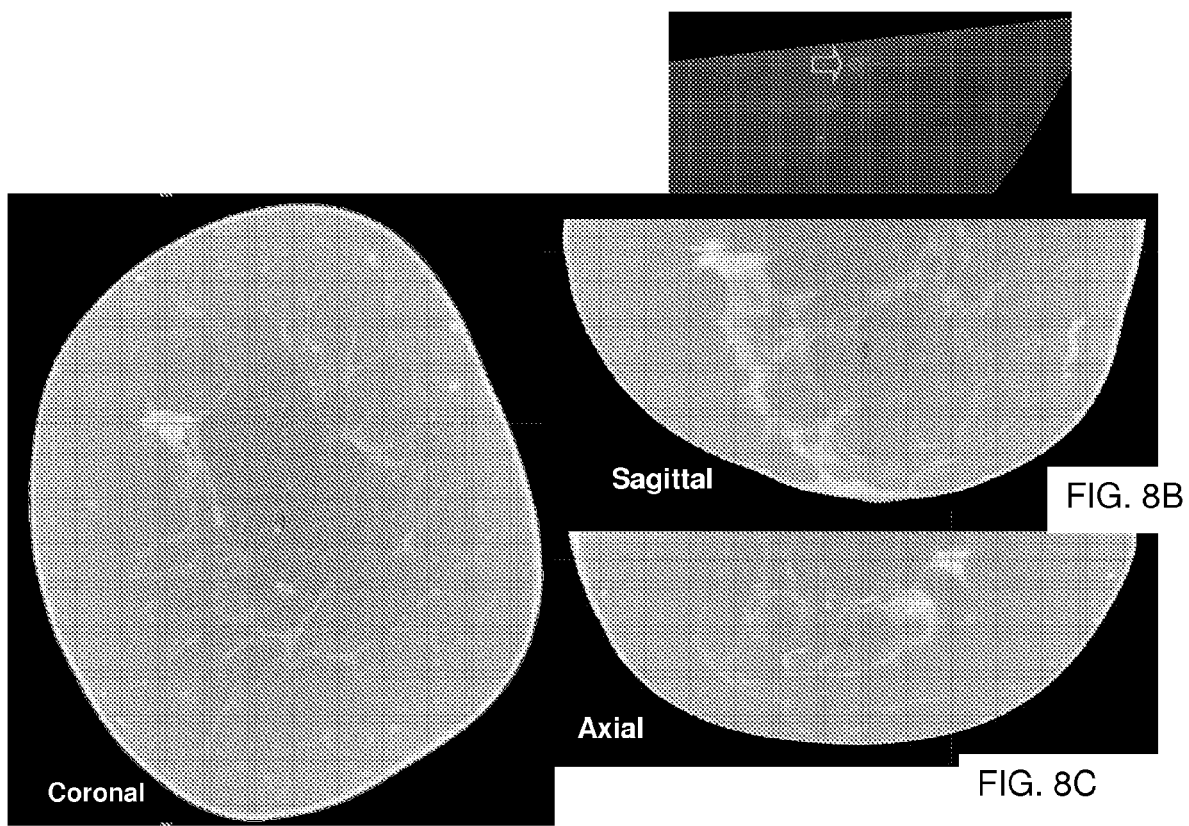
FIGS. 8A-8C are coronal (FIG. 8A), sagittal (FIG. 8B) and axial (FIG. 8C) images of a patient's left breast showing two orthogonal lines crossing the approximate center of the 10 mm contrast-enhanced lesion in accordance with one embodiment of the present invention, with the upper right portion of FIG. 8 being one view of the volume rendered set illustrated in FIG. 5, where the pink block arrow points to the feature centered in the cross-lines of FIGS. 8A-8C.

In one aspect, the present invention provides a method of identifying cancer lesions in the CT images. Traditionally, a mammographer or a radiation physicist spent hours in reviewing all the data available that eventually led to a clear malignancy identification. According to one embodiment of the present invention, the signal ranges for the contrast-enhanced lesions, the benign glandular tissues, and the skin boundary are defined as described above and shown in FIG. 4 (e.g., 1850-2100 for iodine contrast-enhanced lesions, 1560-1700 for benign glandular tissue, and $-350$ for the skin boundary for this specific case of data scaling and offset). The approximate centers of each of the six contrast-enhanced volumes are identified by quickly scrolling through the three orthogonal slice directions (coronal, sagittal and axial where these directions here are defined relative to a standard, horizontal rotation axis of a ring CT gantry and supine or prone patient lying on a support). The surface rendering provides a red perimeter band (color selected arbitrarily) around these orthogonal slice lesion boundaries. Manual scrolling and such identification takes about one minute to produce the end results, as shown in FIGS. 7A-7C. This is for the largest 10 mm lesion but the outlines of the 6 mm and 4 mm lesions are also highlighted with red boundaries in FIGS. 7A-7C. For presentation and reading, these red boundaries can be removed so that the orthogonal images (centered here through the largest 10 mm lesion) are presented in the gray scale format most familiar to radiologists, as shown in FIGS. 8A-8C. The dotted lines indicate the approximate center of the largest lesion. For reference, the pink arrow in the surface rendered image in the upper right of FIGS. 8A-8C points to the exact surface-rendered lesion being imaged. These orthogonal images shown in FIGS. 8A-8C provide high resolution and clear details not available from standard, compressed breast, projection mammography images. If desired, each of the 3 orthogonal images can be shown on 3 separate display screens for maximum viewing spatial resolution, while the reference locating image on the top right of FIGS. 8A-8C can be superimposed on any of the 3 screens or displayed on a separate fourth screen.

One method for quickly calculating the approximate center of a mass by computer is to pick one point well inside each of the three red perimeters of the three orthogonal images of FIGS. 7A-7C. From these 3 points, construct 12 lines passing through each point but each rotated 45 degrees from the other. The resulting x, y and z values of the 24 intersections of these lines with the red perimeters (8 intersections on each orthogonal projection) can then be used to calculate the mean or median values for all 24 x, y and z values. This mean or median x, y and z value can then be used to quickly estimate the center of the mass.

Another method for quickly identifying the location of suspected cancer lesions from large CT data sets is as follows. Refer to FIGS. 7A-7C, the planes of coronal, sagittal, and axial are taken as perpendicular to the x, y and z orthogonal axes respectively. Using the Eclipse™ or comparable software, the coronal images are scrolled through until a surface-bordered (e.g. red-rendered) suspicious lesion is visually identified (as illustrated for example in FIG. 7A). The user then scrolls slowly just in the region where this suspected lesion's boundaries are shown, and the CT slice image that has approximately the largest area inside the red boundary is selected. This x value for this specific coronal plane provides the reference value $x_r$. The user then places the cursor arrow in the roughly center of this boundary and clicks on this point to identify the reference $y_r$ and $z_r$ values. These $x_r$, $y_r$ and $z_r$ values are then used to display the orthogonal (coronal, sagittal, and axial images) slices through the suspected lesions (as illustrated in FIG. 8A). Eclipse™ or similar software can then be used, to move slightly back and forth through any (or all or a combination) of slice directions to more clearly visualize the suspected lesion (with or without the reference cross lines shown in FIG. 8A). If volume-rendered CT data are used, the process is the same except that cross sectional area of the suspected lesion is displayed rather than just its boundary. Its approximate largest cross sectional area is used to define $x_r$. Cursor clicking in the approximate center of the $x_r$ plane gives $y_r$ and $z_r$. For illustration, only the coronal slice direction is described. However, any other slice directions can be used to perform this reference identification, including the sagittal and axial directions or directions oblique to them. The rocking, back and forth viewing can be done with or without the surface or volume-rendered regions being shown in color. The above described process can be done entirely automatically with a computer program. The computer program goes through the images slices in some specified plane direction (like coronal) and identifies a plane where the area in the contrast-enhanced region is approximately maximized and $x_r$, for example, is identified. The program then identifies the approximate center of the enhanced region (center of mass, median values of the intercepts of multiple lines, drawn through this area, etc) to specify for example $y_r$ and $z_r$. The program then automatically displays the appropriate images (like FIGS. 8A-8C) in near real time and free from human interaction. If desired, the viewer can then do the rocking, back and forth viewing as desired.

Figures 9A, 9B, 9C:
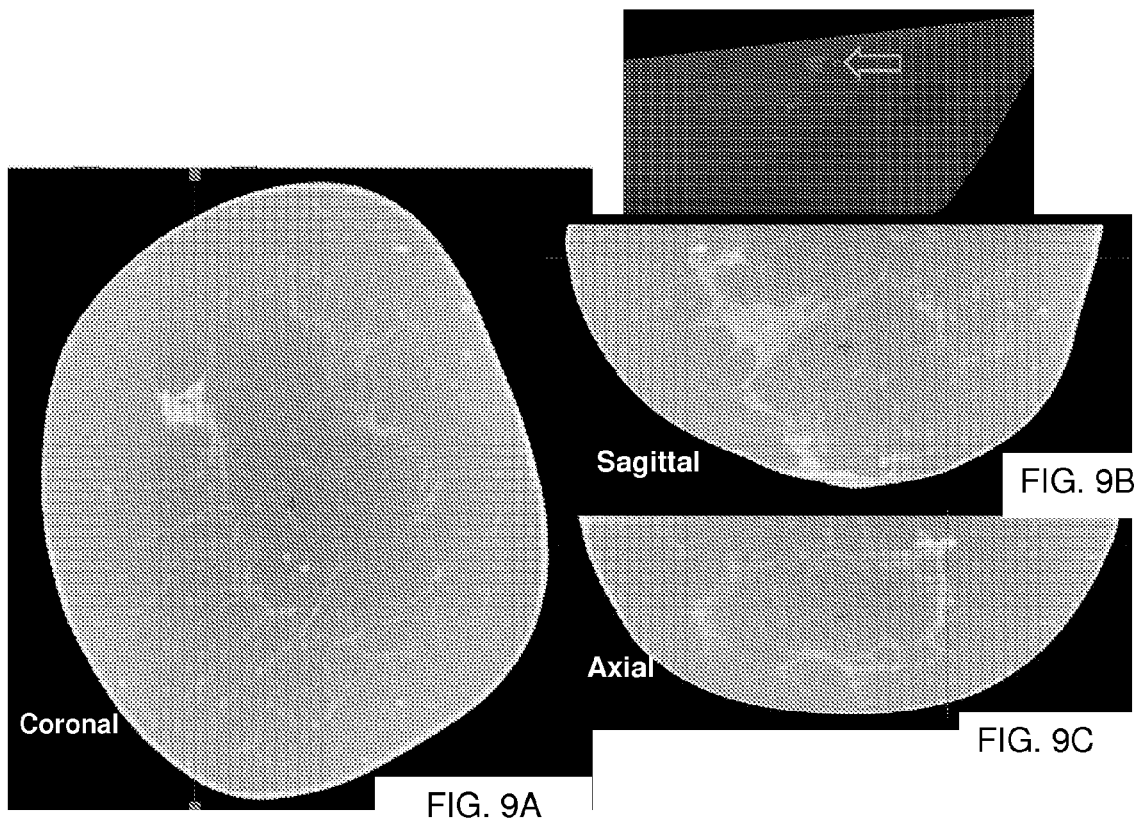
FIGS. 9A-9C are coronal (FIG. 9A), sagittal (FIG. 9B) and axial (FIG. 9C) images of a patient's left breast showing two orthogonal lines crossing the approximate center of the 4 mm contrast-enhanced lesion in accordance with one embodiment of the present invention, with the upper right portion of FIG. 9 being one view of the volume rendered set illustrated in FIG. 5, where the pink block arrow points to the feature centered in the cross-lines of FIGS. 9A-9C.

FIGS. 9A-9C show the orthogonal, grey scale images of the 4 mm lesion. The satellite malignancy, extending away from the large 10 mm lesion, is clearly defined in three dimensional space so that its tissue can be removed with excision processes such as lumpectomy without inadvertently leaving behind cancerous tissues not easily defined in standard mammography projection imaging. FIGS. 9A-9C also clearly show the relationship between the 4 mm lesion with the surrounding benign glandular tissue, particularly in FIG. 9B showing the sagittal view.

FIGS. 10A-10C show contrast-enhanced images for the 1.4 mm lesion. Here, the indicated region has a total volume over 300 times less than that of the 10 mm lesion. Thus, a malignancy as small as 1.4 mm can be resolved with the method of the present invention.

Figures 11A, 11B, 11C:
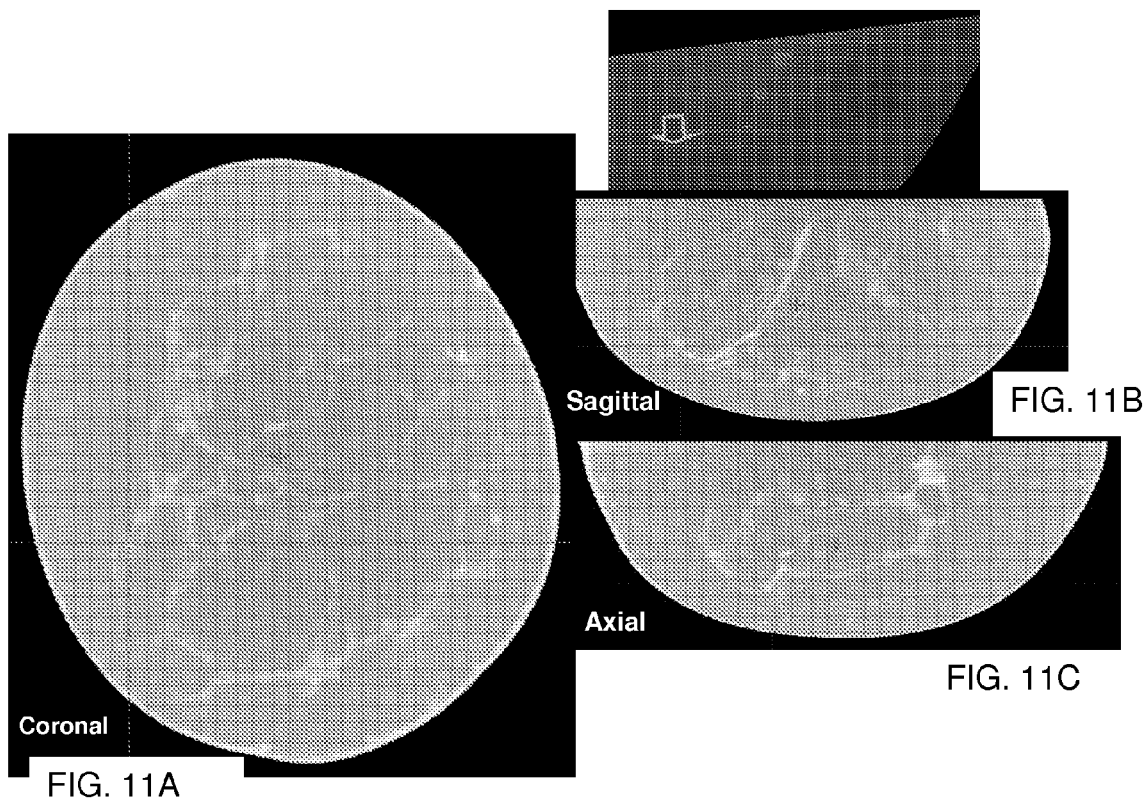
FIGS. 11A-11C are coronal (FIG. 11A), sagittal (FIG. 11B) and axial (FIG. 11C) images of the patient's left breast showing two orthogonal lines crossing the approximate center of the 1 mm contrast-enhanced lesion in accordance with one embodiment of the present invention, with the upper right portion of FIG. 11 being one view of the volume rendered set illustrated in FIG. 5, where the pink block arrow points to the feature centered in the cross-lines of FIGS. 11A-11C.

FIGS. 11A-11C show contrast-enhanced images for the 1 mm lesion. The total volume of the 1 mm lesion is about 1000 times less than that of the 10 mm lesion. Gd-enhanced MRI imaging starts running into serious false positive problems for lesions with linear dimensions of 5 mm or less. The contrast-enhanced CBCT as described in the present invention provides higher spatial and time resolutions than Gd-MRI and is useful in differentiating small enhanced benign regions from malignant ones.

Figures 12A, 12B, 12C:
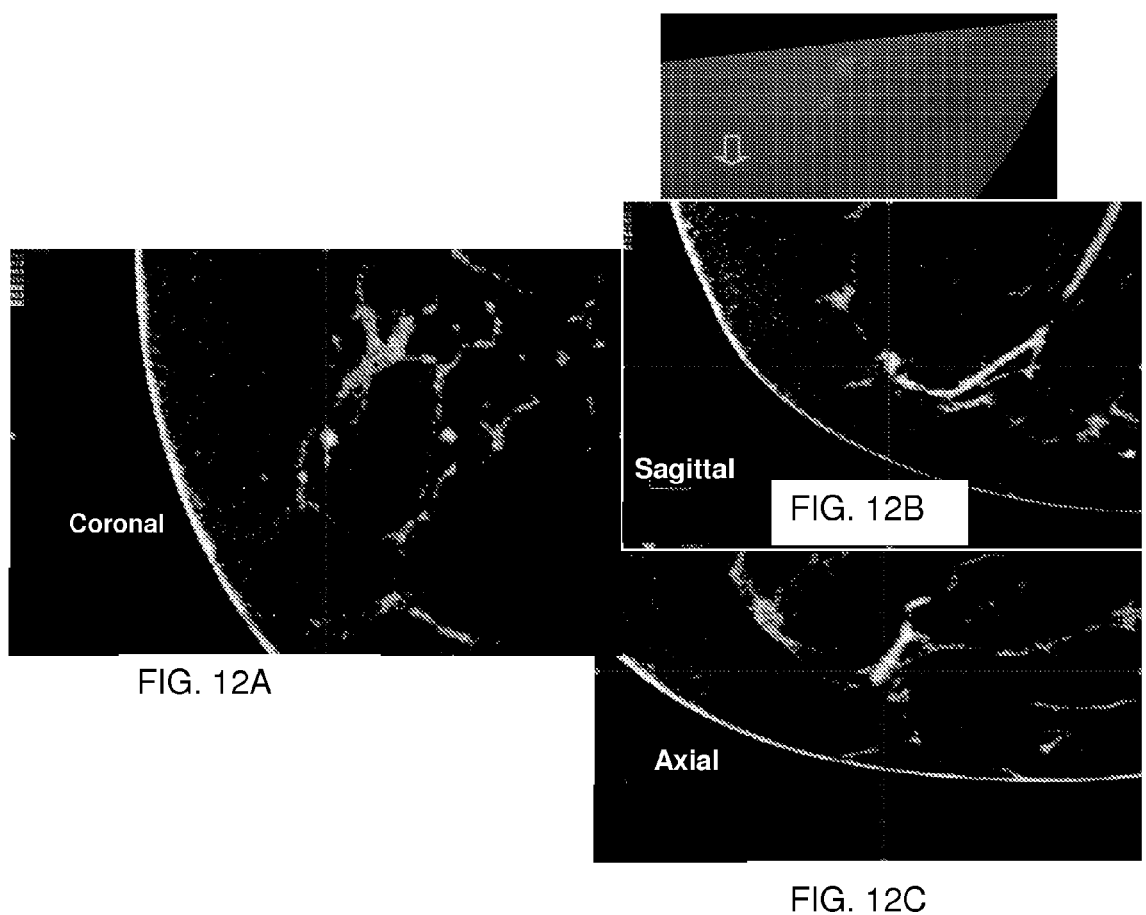
FIGS. 12A-12C are magnified (4×) views of the coronal (FIG. 12A), sagittal (FIG. 12B) and axial (FIG. 12C) images of a patient's left breast illustrated in FIGS. 11A-11C, with the upper right portion of FIG. 12 being one view of the volume rendered set illustrated in FIG. 5, where the pink block arrow points to the feature centered in the cross-lines of FIGS. 12A-12C.

The extra versatility offered by the spatial and contrast resolution of the present invention is illustrated in FIGS. 12A-12C, where the images in FIGS. 11A-11C are magnified by ~4× and their window and leveling narrowed to just show the glandular, contrast-enhanced, and skin regions. This likely provides useful differentiation information. The 1 mm potential lesion region is so small in the images that its enhanced cross sections only appears here as dots.

The contrast-enhanced CBCT of cancer lesions with high spatial and time resolution is highly desirable. There is a strong need for accurate quantitative methods for characterizing cancer growths from their earliest stages so that various cancer initiation and growth can be investigated. While the present invention is not limited to any theories, it is proposed (J. Folkman, Tumor Angiogenesis, in Cancer Medicine, 5$^{th}$ Edition, J. Holland and E. Frei, Eds, Decker, London, pp. 134-137, 2000) that pre-angiogenic tumors are limited in size to 0.2 to 2 mm in diameter which suddenly switch to a rapid growth mode (phenotype) that includes angiogenesis. This model proposes that a large tumor mass inhibits this "switching" of these small pre-angiogenic masses until this primary tumor is removed. Once this primary tumor and its inhibition are absent, these "secondary" pre tumors and/or metastases "switch" into their rapid growth phase with angiogenesis. The excellent time and spatial resolutions and the sensitivity provided by the contrast-enhanced CBCT of the present invention is well suited for testing this model, as evidenced in FIGS. 4-12 showing numerous small contrast-enhanced regions and potential malignancies in a patient with breast cancer. The high expectations for improved cancer therapy with angiogenesis inhibitors predicted in the 1990's are largely unconfirmed through 2005 (C. Sturk and D. Dumont, Angiogenesis, in The Basic Science of Oncology, $4^{th}$ Edit., I. Tannock et al Eds., McGraw-Hill, New York, p. 244, 2005). This is due at least in part to lack of understanding of the timing and effects of these agents on cancer biology and functioning. The latter is needed for better coordination, scheduling and timing with adjuvant cancer therapies, including cytotoxic chemotherapy, radiation therapy, hormone therapy and surgery. The contrast-enhanced CBCT with high spatial and time resolution provided by the present invention eliminates at least some of the uncertainties and provides the basis for defining improved protocols for the delivery of combined adjuvant cancer therapies.

The initiation, growth, diagnosis, staging and successful treatment of cancer is a highly varied and complex biological, chemical and physical process. However there appear to be three fundamental physical and chemical processes that underlie and that are essential to the growth, functioning, development, and the monitoring and assessment of optimal treatments of all solid cancer lesions. The first fundamental process is the biochemical metabolism of life, with in-diffusion of nutrients like oxygen and glucose, and the out-diffusion of waste products like $CO_2$ over a maximum distances of 100 to 200 μm to and from blood supplies to and from most human (and animal) cells (R. Sutherland, Science, Vol. 240, pp. 177-184, 1988; J. Folkman, Tumor Angiogenesis, in Cancer Medicine, $5^{th}$ Edit., J. Holland and E. Fei Eds., Decker, London, p. 134, 2000). This is required for the rapid growth of any tissue material, including cancers, and requires that capillary blood transport structures (with 10 to 15 μm typical inner diameters in healthy tissues) penetrate throughout such rapidly growing masses with mean spacing on the order of 100 to 200 microns. The second fundamental process is that the rapid growth of cancer is very disordered and unorganized and it initially does not incorporate sufficient capillary structures. The result is that stress, such as low oxygen concentrations or hypoxia, develops in the cells of undersupplied regions of the cancer. This stress triggers local genes to produce (express) proteins (including vascular endothelial growth factor or VEGF) in these areas, which then out-diffuse and initiate the sprouting of new capillary tubes toward the stressed regions from the preexisting capillaries. However, the resulting new tubes have very distinctive geometries that are random, disordered, tangled, truncated and larger diameter as compared to the highly ordered geometries of healthy regions. The third fundamental process is that these stress-induced new capillary tubes largely consist of just the linings (endothelia) of blood vessels without the basal membranes and smooth-muscle-outer coatings, which are present in the healthy, more intact capillaries. A critical result is that the walls of these substandard tubes are very leaky, and in particular tend to leak out contrast agents such as gadolinium or iodine containing compounds into the tissues surrounding them. Typically this occurs in sufficient concentrations that the cancer structures can be readily imaged with contrast-enhanced X-ray cone beam CT as described herein.

In addition for the visualization of the shape and size of contrast-enhanced volumes and their longer term (days to weeks to months) changes with time, there are additional characteristics useful to the detection, monitoring, assessment and treatment of cancer. These additional characteristics derived directly from contrast-enhanced cone beam CT include the shorter term (minutes to seconds) measured kinetics that quantify tissue perfusion, relative blood volume, capillary permeability and leakage space as described using compartmental analysis and deconvolution normalized by time-attenuation-data of the arterial system to correct for interpatient variations in bolus geometry. Perfusion is calculated from the maximal slope of the tissue concentration-time curve (of the contrast media) or from its peak height, normalized to the arterial input function. Further normalizing perfusion with the ratio of cardiac output to body weight, gives the standardized perfusion value. Extending this to a two compartment model determines the capillary permeability and the blood volume. Deconvolution is an alternate approach to the same parameters. It uses the arterial and tissue concentration-time curves to calculate the impulse residue function (IRF). The IRF is a theoretical tissue curve that would be obtained from an instantaneous arterial input. The height of the flow corrected IRF gives the tissue perfusion and the area under the curve determines the blood volume. Use of a distributed parameter model extends this analysis to provide a measurement of capillary permeability. All these parameters are useful in oncology for diagnosis, staging, assessment of tumor grade and prognosis and for therapy monitoring. The present invention uses a monolithic and integrated-pixels sensor array to provide high spatial resolution images of larger volumes with seconds-level time resolutions, with reasonable X-ray doses and with affordable component and systems costs.

In some embodiments, a high spatial resolution of images can be obtained by using magnification and/or small X-ray spot size of the X-ray source to clearly differentiate cancerous tissue from benign tissues based on contrast agent enhanced CBCT or CBDT. Magnification ratio (X) is defined as a ratio of the distance from the X-ray source to the flat panel imager to the distance from the X-ray source to the patient. For low magnification ratio approaching 1, the spatial resolution is largely determined by the spatial resolution of the imager itself, which is the imager's pixel size, degraded by any blurring in the scintillator, if any. For high magnification ratio (>10), the spatial resolution is largely determined by the spot size of the X-ray source. For intermediate magnification X values, the resulting spatial resolution is determined by the combination of the spatial resolution of the imager and the spot size of the X-ray source, often approximated as the square root of the sum of the squares of the two.

Figure 13:
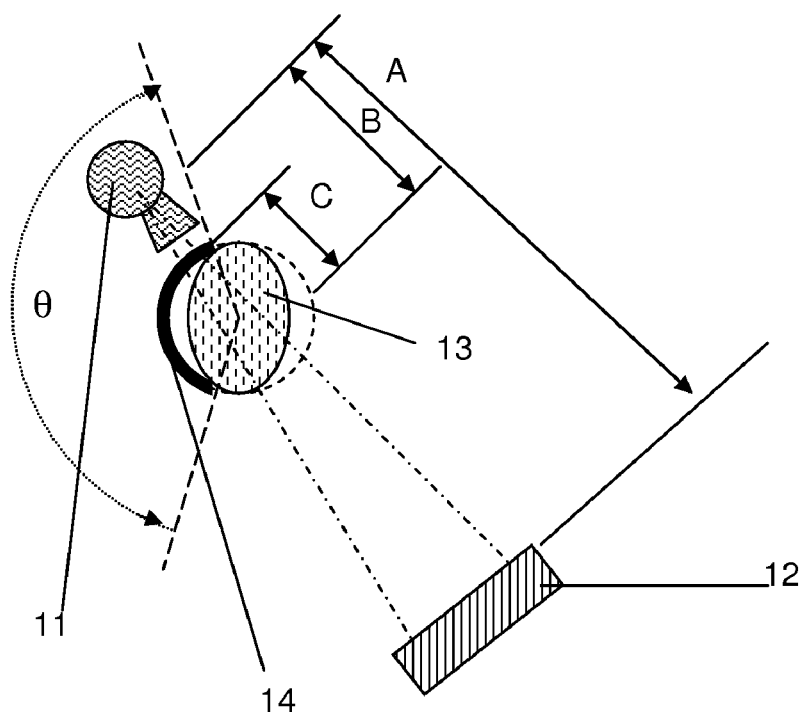
FIG. 13 is a schematic diagram illustrating an X-ray imaging system in accordance with one embodiment of the present invention.

FIG. 13 shows preferred embodiments for different magnifications X. The fixed distance A is measured from the X-ray spot of the X-ray source 11 to the flat panel imager 12. The fixed distance B is measured from the X-ray spot of the X-ray source 11 to the center of rotation about the patient 13 or the patient's part (e.g. the patient's breast). The center of rotation is roughly in the center of the patient 13 or the patient's part. The distance C is measured from the center of rotation out far enough to just clear that part of the patient 13 whose distance from the center or rotation is maximum. The outer surface of the patient support 14 has a cylindrical shape that allows the X-ray source 11 to rotate and angle (θ) around the patient 13 (or patient part) and clear it by a small margin (e.g. 1 cm). The approximate magnification is A/B~X. Preferred values for these parameters are listed in Table 1. The spot size of the X-ray source 11 is approximately the spatial resolution of the cone beam CT data set because the spot of the X-ray source 11 is placed close to the center of rotation, compared to distance of this spot to the flat panel imager 12. Exemplary preferred X-ray source spot sizes include diameters of 800, 400, 200, 100, 70, 50, 30, 10, 1, 0.1 and 0.02, all measured in microns. At the larger magnifications with low angle (θ) □values (<15°), the motion of the X-ray source 11 and the flat panel imager 12 can be the straight line cords across their respective circular paths but in opposite directions, since these well approximate circular paths for such small angles. For the most general embodiment, the motion can be any relative motion (linear, curved, zig-zag trajectories), with motion by either the source 11 or the imager 12 or both, as long as multiple X-ray beams from the source pass through all of the voxels of the patient's 13 region of interest, at multiple and known angles.

TABLE 1

| A (cm) | B (cm) | C (cm) | X | θ | Embodiments |
|---|---|---|---|---|---|
| 24 | 12 | 6 | 2 | 365° | Small patient part like breast |
| 36 | 12 | 6 | 3 | 365° | Small patient part like breast |
| 60 | 12 | 6 | 5 | 365° | Small patient part like breast |
| 120 | 12 | 6 | 10 | 186° | Small patient part like breast |
| 300 | 10 | 6 | 30 | 60° | Small patient part like breast |
| 900 | 9 | 6 | 100 | 20° | Small patient part like breast |
| 8000 | 8 | 5 | 1000 | 5° | Small patient part like breast |
| 75 | 25 | 20 | 3 | 365° | Full size patient part like torso |
| 125 | 25 | 20 | 5 | 186° | Full size patient part like torso |
| 250 | 25 | 20 | 10 | 70° | Full size patient part like torso |
| 660 | 22 | 18 | 30 | 35° | Full size patient part like torso |
| 2100 | 21 | 17 | 100 | 8° | Full size patient part like torso |
| 19,000 | 19 | 16 | 1000 | 4° | Full size patient part like torso |

Figure 14:
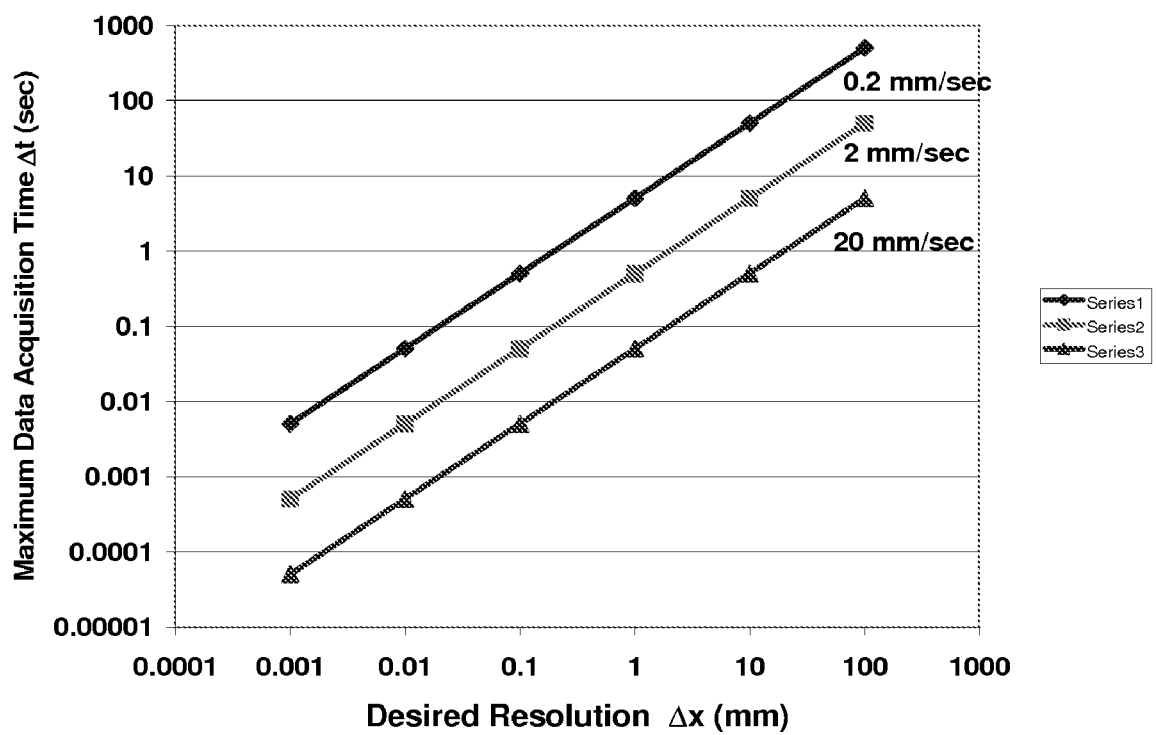
FIG. 14 is a plot illustrating the time interval for acquiring image data sets as a function of desired resolution.

To achieve a given spatial resolution $\Delta x$ when the region of interest is moving at a velocity v, the image acquisition data set needs to be taken in a time interval $\Delta t$ where the distance moved is less than the resolution desired. This is expressed as $\Delta t \leq \Delta x/v$. The maximum value of the $\Delta t$ expression as a function of the desired resolution $\Delta x$ is plotted in FIG. 14 for velocities of 0.2, 2.0 and 20 mm/sec. These velocities are representative of the repetitive (e.g. respiratory and cardiac) and random (e.g. peristalsis) motion often encountered in humans. This $\Delta t$ can be the time to collect the total tomography data set or can be the time for one interval of a gated data set, where one waits (or gates) until the moving region of interest is positioned between defined limit positions and the $\Delta t$ is then the maximum time to acquire the data per such gated interval. For more confidence in achieving a given spatial resolution, the maximum can be reduced by a factor of 3 to $\Delta t \leq \Delta x/(3v)$.

The trade off of high magnification is that the flat plate imagers still need to receive about the same total X-ray doses from the source, as required for similar contrast resolutions at low or no magnification. The X-ray dose output from X-ray sources decrease proportionally to the decrease in their spot sizes. Simultaneously, the dose per unit volume goes up dramatically since the volume imaged goes down with the cube of its linear dimension. A result is that the dose densities can be come too high and alter or damage the region being imaged. The latter is particularly problematic in volumes consisting of healthy, benign tissues. A preferred embodiment that addresses this issue is the use of a flat panel imager or a tiled discrete pixel imager that can photon count the X-ray signals absorbed in each pixel and provide pulse-height signals that characterize the energy distribution of the X-ray photons absorbed in each pixel. This can eliminate all the electronic noise from the acquired data and allow lower dose levels where the noise is only limited by the quantum statistics of the X-ray photons in each pixel. Further, the energy discrimination allows the signal at each pixel to be segmented into as many energy segments as desired. Thus the signal with energies just above and below the characteristic absorption edge can be established with any desired energy band width to resolve the presence or absence and the concentration of contrast agent of any voxel in the 3D data set for even lower dose imaging. Once clear discrimination has been established, the dose density to the malignant portions of the volume image can be selectively increased back up to therapeutic levels, to provide treatment simultaneously as such cancer regions are imaged with CBCT and/or CBDT. Once this or any other therapy has been delivered, the low dose, non-therapeutic, contrast-enhanced imaging can be repeated to monitor the response to therapy for time frames ranging from milliseconds to months following or during treatments.

In one specific embodiment, an X-ray dose ranging from 2-50 milligray is used in acquiring two-dimensional projection images for a cone beam tomography data set. In another specific embodiment, an X-ray treatment dose distribution ranging from 1-7000 centigray is delivered to the uncompressed region of interest to treat the cancer tissue identified. The treatment dose may be delivered during or after the reconstruction of the three-dimensional images data set that resolve the cancer tissue.

A preferred treatment procedure and system configuration are as follows. A small malignancy ($\leq$7 mm diameter, either a primary tumor or a metastasis) is identified from surface-rendered, iodine contrast-enhanced, cone beam CT data sets as described above, using enough magnification (30× or greater) that a large fraction of a Varian PaxScan4030CB image sensor plate (with pixels that measure 194 μm on a side) is filled with the image of the lesion. The kilovoltage X-ray source spot size is low enough (<0.2 mm diameter) so that this spot size does not seriously limit the spatial resolution of the cone beam CT image data set. A suitable motion management system such as Varian RPM™ System is used to control the cone beam CT image data acquisition so the X-ray source is only on when the lesion is in the right position for radiotherapy treatment so that a complete rotational cone beam CT data set is acquired, free of most motion artifacts. The shape of the beam from the X-ray source is controlled by a micro-multileaf collimator to match the boundary of the lesion, plus a specified margin (e.g., 1 mm), from every rotation angle that a projection image is acquired. As each cone beam data set is obtained, the beam current of the X-ray source is adjusted to a level that the desired radiotherapy dose is delivered to this lesion with the X-ray source constantly moving (relative to the patient and the lesion) to spread out the dose to the healthy tissue surrounding the lesion and to reduce the patient's skin dose. This dose can be delivered in a single (or partial) rotation or in multiple successive rotations, in a single session (or dose fraction) to achieve the higher dose levels that may sometimes be desired. This process is repeated for every dose fraction that typically are once daily, 5 days a week, spanning 4 to 6 consecutive weeks, for typical fractionated dose delivery protocols. Since the imaging is being performed during radiotherapy (plus any simultaneous adjuvant hormone or chemotherapy), the contrast agent is added at appropriate intervals (e.g., at 5 equally spaced periods) over the whole dose delivery period. The latter is used to monitor the angiogenesis' (and the enhanced contrast kinetics parameters') response to the therapy and adapt the (radio and/or chemo and/or hormone) therapy to the changes that occur during the treatment period, including changes in the shape and size of the lesion. This can be repeated, for multiple lesions during a single 4 to 6 week fractionated treatment period protocol, as desired.

Another preferred treatment procedure and system configuration is the same as immediately above except that the X-ray source is a megavoltage one (e.g., 6 MeV). The contrast resolution goes down at megavoltages (compared to kilovoltages) but it is still good enough (2% or better) to distinguish many lesions and their properties. An advantage of megavoltage is that the dose energy delivered per absorbed X-ray photon is much higher, so that the beam current required and the dose delivery time can be much lower than with kilovoltage sources.

In some embodiments, the X-ray source 11 is a quasi-monochromatic source that provides higher sensitivity for contrast enhanced CBCT and CBDT at lower X-ray doses. It consists of a distributed array of single crystal elements (or lamella) that capture a larger fraction of the beam emitted from high power X-ray tubes like the Snowbird tube available from Varian Medical Systems, Inc. It is tunable over the standard diagnostic X-ray energy range (30-100 kVp) and has a bandwidth on the order of several eV. This embodiment captures a large solid angle of X-rays from a small projected area source. It has high efficiency for a narrow band of X-ray energies. The configuration has crystal lamella mounted onto a specified surface shape, according to specified design requirements. Combined with standard X-ray tubes, it has numerous applications where high efficiency and capture of narrow energy band X-rays are vital. It can be used to improve numerous CBCT and CBDT procedures and make new ones possible. The configuration can be used to alter the characteristics of the X-ray beam from the source. This includes providing a smaller effective source diameter or a parallel instead of divergent beam. It provides specifications to select and bend the beam from an X-ray tube source 11 to produce nearly mono energetic X-ray beams with divergence from either, virtual or real focal spots, located at various positions, relative to the source spot. The basic concept is the simultaneous use of both the diffraction plane orientations and the crystal lamella's mosaic and positions to achieve mono chromaticity and high capture efficiency.

In some embodiments, the X-ray source 11 is a quasi-monochromatic source for specific use with the contrast enhanced CBCT and CBDT at lower X-ray doses.

The quasi-monochromatic source has 200 to 500 attenuation value layer films of elements that include cerium, neodymium, europium and tungsten, with respective K-edge absorption peak energies or 40.44, 43.57, 48.52, and 69.53 keV, with respective $200^{th}$ value layer thickness of 0.71, 0.7, 1.00, and 0.2 mm, with respective $500^{th}$ value thickness of 0.91, 0.93, 1.25, and 0.25 mm, placed in the beam of an X-ray tube operating in the 40-100 kVp range so that the value layer films serve and narrow band X-ray filters.

In some embodiments, the X-ray source 11 is a quasi-monochromatic source for specific use with the contrast enhanced CBCT and CBDT at lower X-ray doses. The quasi-monochromatic source has multilayer films of high and low X-ray density materials that serve as tunable, narrow band X-ray filters, that are placed in the beam of an X-ray tube operating in the 40-100 kVp range.

In one aspect of the present invention, angiogenesis inhibiting treatments (including drugs) or any other cancer treatments are performed on a patient, and then the angiogenesis response, and the kinetics parameters of the injected contrast medium as surrogates for the response to treatment are monitored. Such angiogenesis inhibiting drugs include Avastin (bevacizumab), Angiostatin, Arresten, Canstatin, Combretastatin, Endostatin, NM-3, Thalidomide, Thrombospondin, Tumstatin, 2-Methoxyestradiol, Vitaxin, Iressa, Tarceva, Erbitux, Gleevec, Herceptin, Interferon-α, Su 11248, Bay 43-9006, AG-013736, PTK787 and SU5416. Development and optimization of these combination therapies can be greatly enhanced by the ability to image changes in the tumor blood vessels using the invention described herein. This imaging procedure includes collecting the images over time up to 20 to 30 minutes after the injection of the contrast agent. This provides information about the therapy induced changes over the course of treatment. These images will provide information on structural changes as well as pathophysiological effects.

Various schedules for combining these antiangiogenic or antivascular agents with drugs and/or radiation can be developed with the use of the present imaging method, that is, the optimal sequence and timing. It has been proposed that these drugs that act on blood vessels can 'normalize' the vasculature (R. Jain, Science, Vol. 307, pp. 58-62, 2005). This 'normalization' involves changes in vessel pattern structure, size and permeability which can be monitored over time by the imaging method described herein. Synergistic effects with radiation can be achieved by administering drugs or radiation therapy over a defined time window after (or before or during) the antiangiogenic or antivascular therapy.

The present invention provides methods and systems for non-intrusively imaging the angiogenesis effects in solid cancer lesions in vivo with sufficient time and spatial resolution and sensitivity to identify, diagnose, stage, and monitor cancer formation and growth at a significantly earlier stage and with increased accuracy than previously possible. Since early detection and treatment are keys to long term cancer survival, this is an important advantage. Moreover, the present method can be carried out at X-ray doses comparable to those of standard X-ray screening and diagnostic procedures.

From the foregoing it will be appreciated that, although specific embodiments of the invention have been described herein for purposes of illustration, various modifications may be made without deviating from the spirit and scope of the invention.

What is claimed is:

1. A method of imaging a patient's uncompressed region of interest using X-ray cone beam computed tomography (CBCT) or cone beam digital tomography (CBDT) comprising the step of generating a three-dimensional computed tomography image data set of the uncompressed region of interest with a spatial resolution resolving voxels with dimensions of 5 μm or less in at least two orthogonal directions.

2. The method of claim 1 further comprising the steps of:
   introducing an effective amount of a contrast agent to the uncompressed region of interest; and
   acquiring a plurality of two-dimensional projection images for the three-dimensional computed tomography image data set using X-ray computed tomography or digital tomography where one or more of the projection images are acquired in 35 milliseconds or less.

3. The method of claim 2 wherein the one or more of the projection images are acquired in 0.1 milliseconds or less.

4. The method of claim 2 wherein about 500 projection images for the three-dimensional computed tomography image data set are acquired in about 16.6 seconds or less.

5. The method of claim 2 further comprising repeating one or more times the steps of introducing a contrast agent to the uncompressed region of interest and acquiring projection images in a predetermined time interval.

6. The method of claim 1 further comprising the steps of:
   introducing an effective amount of a contrast agent to the uncompressed region; and
   acquiring a plurality of two-dimensional projection images for the three-dimensional computed tomography image data set using a quasi-monochromatic X-ray source.

7. The method of claim 6 further comprising repeating one or more times the steps of introducing a contrast agent to the uncompressed region and acquiring projection images in a predetermined time interval.

8. The method of claim 1 further comprising the steps of:
introducing an effective amount of a contrast agent to the uncompressed region of interest;
acquiring a plurality of two-dimensional projection images for the three-dimensional computed tomography image data set using cone beam computed tomography or cone beam digital tomography; and
delivering an X-ray treatment dose distribution ranging from 1 to 7000 centigray to the uncompressed region of interest.

9. The method of claim 8 wherein the plurality of two-dimensional projection images are acquired using an X-ray dose ranging from 2 to 50 milligray.

10. The method of claim 8 wherein the step of generating the three-dimensional computed tomography image data set is carried out prior to delivering the X-ray treatment dose distribution to the uncompressed region of interest.

11. The method of claim 8 wherein the step of generating the three-dimensional computed tomography image data set is carried out during delivering of the X-ray treatment dose distribution to the uncompressed region of interest.

12. The method of claim 8 further comprising repeating one or more times the steps of introducing a contrast agent to the uncompressed region of interest, acquiring projection images, and delivering an X-ray treatment dose distribution in a predetermined time interval.

13. The method of claim 12 wherein the predetermined time interval corresponds to a fractioned treatment protocol.

14. The method of claim 1 further comprising the step of acquiring a plurality of two-dimensional projection images for the three-dimensional computed tomography image data set using X-ray cone beam computed tomography (CBCT) or cone beam digital tomography (CBDT), wherein one or more of the projection images are acquired in 35 milliseconds or less.

15. The method of claim 14 wherein one or more of the projection images are acquired in 0.1 milliseconds or less.

16. The method of claim 14 wherein the plurality of projection images are acquired using a two dimensional flat panel imager operating at 1000 frames per second or higher.

* * * * *